United States Patent
Delgado

(10) Patent No.: US 10,847,011 B2
(45) Date of Patent: Nov. 24, 2020

(54) GAS DETECTOR FOR DETECTING MULTIPLE GASES

(71) Applicant: Honeywell International Inc., Morris Plains, NJ (US)

(72) Inventor: Alejandra Gonzalez Delgado, Calgary (CA)

(73) Assignee: Honeywell International Inc., Morris Plains, NJ (US)

( * ) Notice: Subject to any disclaimer, the term of this patent is extended or adjusted under 35 U.S.C. 154(b) by 0 days.

(21) Appl. No.: 16/079,839

(22) PCT Filed: Feb. 24, 2017

(86) PCT No.: PCT/US2017/019256
§ 371 (c)(1),
(2) Date: Aug. 24, 2018

(87) PCT Pub. No.: WO2017/147360
PCT Pub. Date: Aug. 31, 2017

(65) Prior Publication Data
US 2019/0073890 A1    Mar. 7, 2019

Related U.S. Application Data
(60) Provisional application No. 62/300,459, filed on Feb. 26, 2016.

(51) Int. Cl.
*G08B 21/12* (2006.01)
*G01N 33/00* (2006.01)
(Continued)

(52) U.S. Cl.
CPC .......... *G08B 21/12* (2013.01); *G01N 33/0065* (2013.01); *G08B 17/117* (2013.01); *G08B 25/008* (2013.01); *G08B 25/14* (2013.01)

(58) Field of Classification Search
CPC .... G08B 21/12; G08B 17/117; G08B 25/008; G08B 25/14; G01N 33/0065
See application file for complete search history.

(56) References Cited

U.S. PATENT DOCUMENTS 6,069,653 A * 5/2000 Hudson ............ G08B 13/19673
340/500
9,612,195 B1 * 4/2017 Friedman ............ G01N 21/3504
(Continued)

FOREIGN PATENT DOCUMENTS

| CN | 204856838 U | 12/2015 |
| CN | 105336121 A | 2/2016 |

(Continued)

OTHER PUBLICATIONS

International Application No. PCT/US2017/019256, International Search Report, dated Jun. 2, 2017, 4 pages.
(Continued)

*Primary Examiner* — Curtis B Odom
(74) *Attorney, Agent, or Firm* — Alston & Bird LLP

(57) ABSTRACT

Embodiments relate generally to systems and methods for controlling the display of a gas detector. A method may comprise receiving sensed data from a plurality of sensors of the gas detector; displaying the received sensed data on a user interface of the gas detector, wherein the user interface comprises a display, and wherein the display includes information for more than one of the plurality of sensors; and changing the display to an alarm screen that includes only the alarm information, when the gas detector is in an alarm or alert mode. A gas detector configured to detect multiple gases may comprise a plurality of sensors configured to detect a plurality of gases and conditions, and a user interface comprising a display configured to display information received from the plurality of sensors.

20 Claims, 5 Drawing Sheets

(51) Int. Cl.
 G08B 25/14 (2006.01)
 G08B 17/117 (2006.01)
 G08B 25/00 (2006.01)

(56) References Cited

U.S. PATENT DOCUMENTS

| | | | |
|---|---|---|---|
| 2015/0068287 A1* | 3/2015 | Wilcox | G01M 3/22 |
| | | | 73/40.5 R |
| 2015/0212034 A1 | 7/2015 | Ansley | |
| 2015/0379848 A1 | 12/2015 | Gallo et al. | |

FOREIGN PATENT DOCUMENTS

| | | |
|---|---|---|
| CN | 205038764 U | 2/2016 |
| EP | 2339556 A1 | 6/2011 |
| GB | 2329542 A | 3/1999 |
| WO | 2017147360 A1 | 8/2017 |

OTHER PUBLICATIONS

International Application No. PCT/US2017/019256, Written Opinion of the International Searching Authority, dated Jun. 2, 2017, 6 pages.
International Application No. PCT/US2017/019256, International Preliminary Report on Patentability, dated Aug. 28, 2018, 7 pages.
CN Office Action, including Search Report, dated Feb. 3, 2020 for CN Application No. 201780025302.
Communication from the Examining Division dated Sep. 11, 2018 for EP Application No. 17708960, 3 pages.
English Translation of CN Office Action dated Feb. 3, 2020 for CN Application No. 201780025302.

* cited by examiner

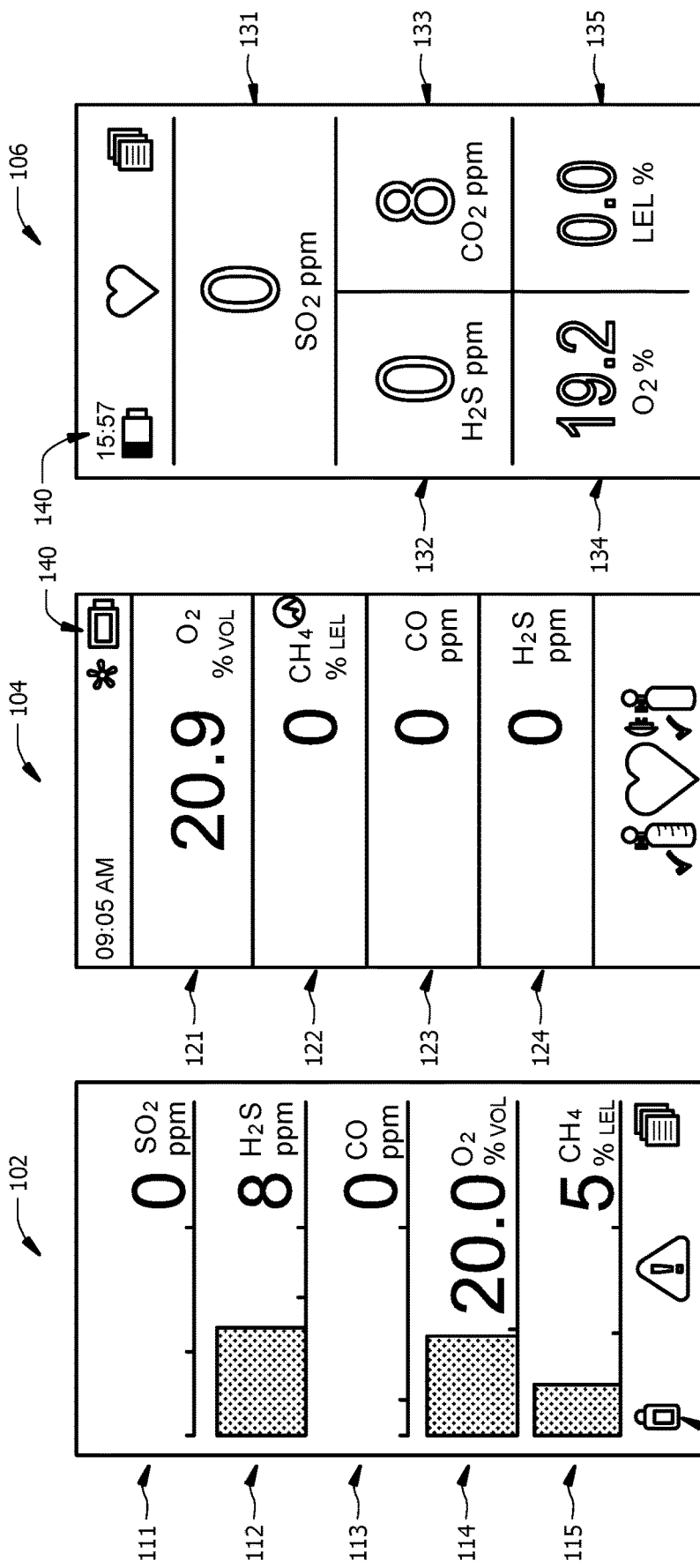

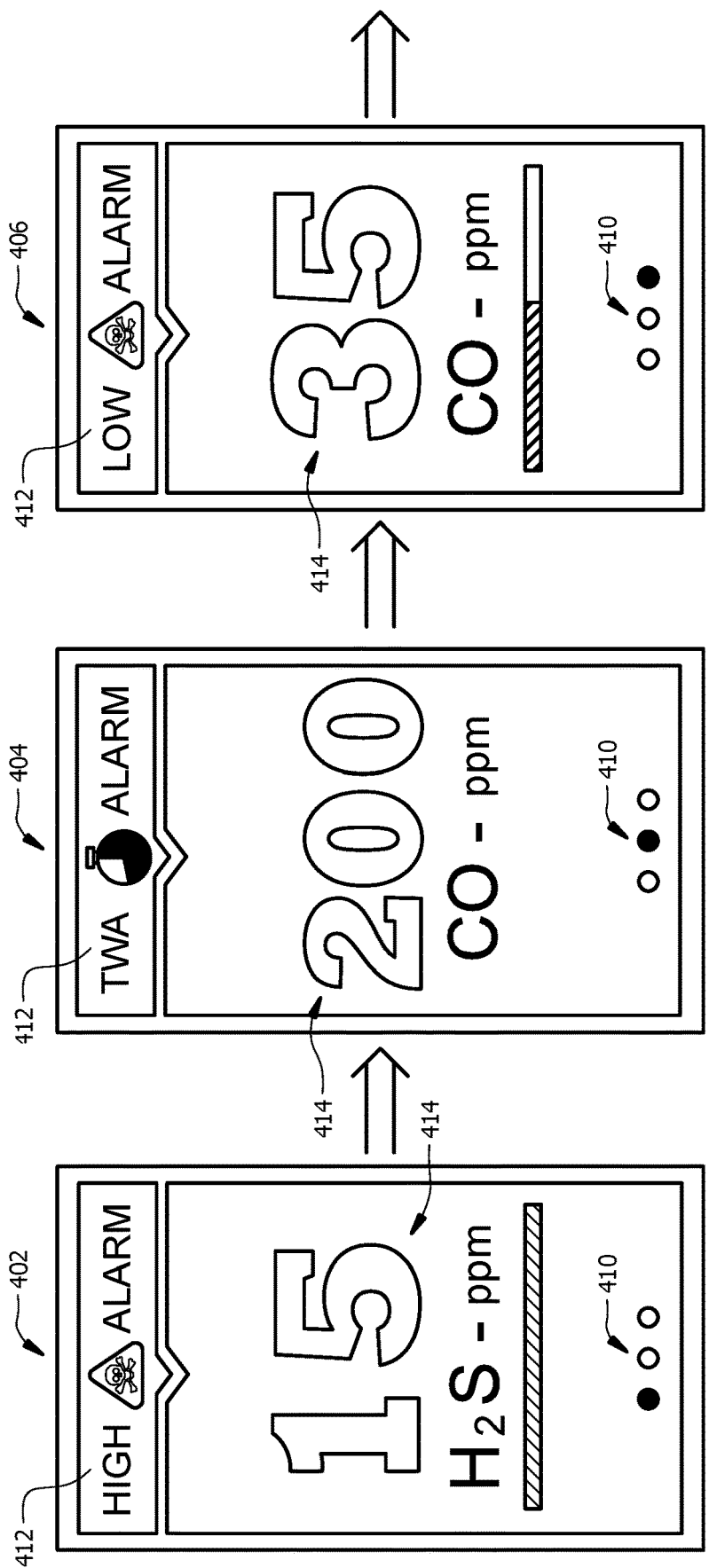

GAS DETECTOR FOR DETECTING MULTIPLE GASES

CROSS-REFERENCE TO RELATED APPLICATIONS

The present application is the National Stage of International Application No. PCT/US2017/019256 filed Feb. 24, 2017 and entitled "Gas Detector For Detecting Multiple Gases," which claims priority to U.S. Provisional Patent Application No. 62/300,459 entitled "Only Alert" filed Feb. 26, 2016, such that the present application claims priority to both listed related applications, both of which are incorporated herein by reference as if reproduced in their entirety.

STATEMENT REGARDING FEDERALLY SPONSORED RESEARCH OR DEVELOPMENT

Not applicable.

REFERENCE TO A MICROFICHE APPENDIX

Not applicable.

BACKGROUND

In hazardous work environments, user may carry gas detectors with them as they work, to allow for detection of gas exposure. The gas detector may alert the user if an exposure limits are reached while the user is wearing the gas detector. Gas detectors may comprise interfaces for communicating with the user, such as displays, lights, buzzers, and input buttons. Gas detectors may be configured with settings for alarms, exposure limits, display settings, light and buzzer settings, etc.

SUMMARY

In an embodiment, a method for controlling the display of a gas detector may comprise receiving sensed data from a plurality of sensors of the gas detector; displaying the received sensed data on a user interface of the gas detector, wherein the user interface comprises a display, and wherein the display includes information for more than one of the plurality of sensors; and changing the display to an alarm screen that includes only the alarm information, when the gas detector is in an alarm or alert mode.

In an embodiment, a gas detector configured to detect multiple gases may comprise a plurality of sensors configured to detect a plurality of gases and conditions; a user interface comprising a display configured to display information received from the plurality of sensors; wherein when the gas detector is in normal operating mode, the display includes information for more than one of the plurality of sensors, and wherein when the gas detector is in an alarm or alert mode, the display changes to an alarm screen that includes only the alarm information.

In an embodiment, a gas detector may comprise a plurality of sensors configured to detect a plurality of characteristics of the ambient environment; a user interface comprising a display; and a controller configured to receive sensed data from the plurality of sensors; display the received sensed data via the display of the user interface, wherein the display includes information for more than one of the plurality of sensors; and change the display to an alarm screen that includes only alarm information, when the gas detector is in an alarm mode.

BRIEF DESCRIPTION OF THE DRAWINGS

For a more complete understanding of the present disclosure, reference is now made to the following brief description, taken in connection with the accompanying drawings and detailed description, wherein like reference numerals represent like parts.

FIGS. 2A-2C illustrate display screens for a gas detector according to an embodiment of the disclosure.

FIGS. 5A-5C illustrate alarm screens for a gas detector according to an embodiment of the disclosure.

DETAILED DESCRIPTION

Figure 1:
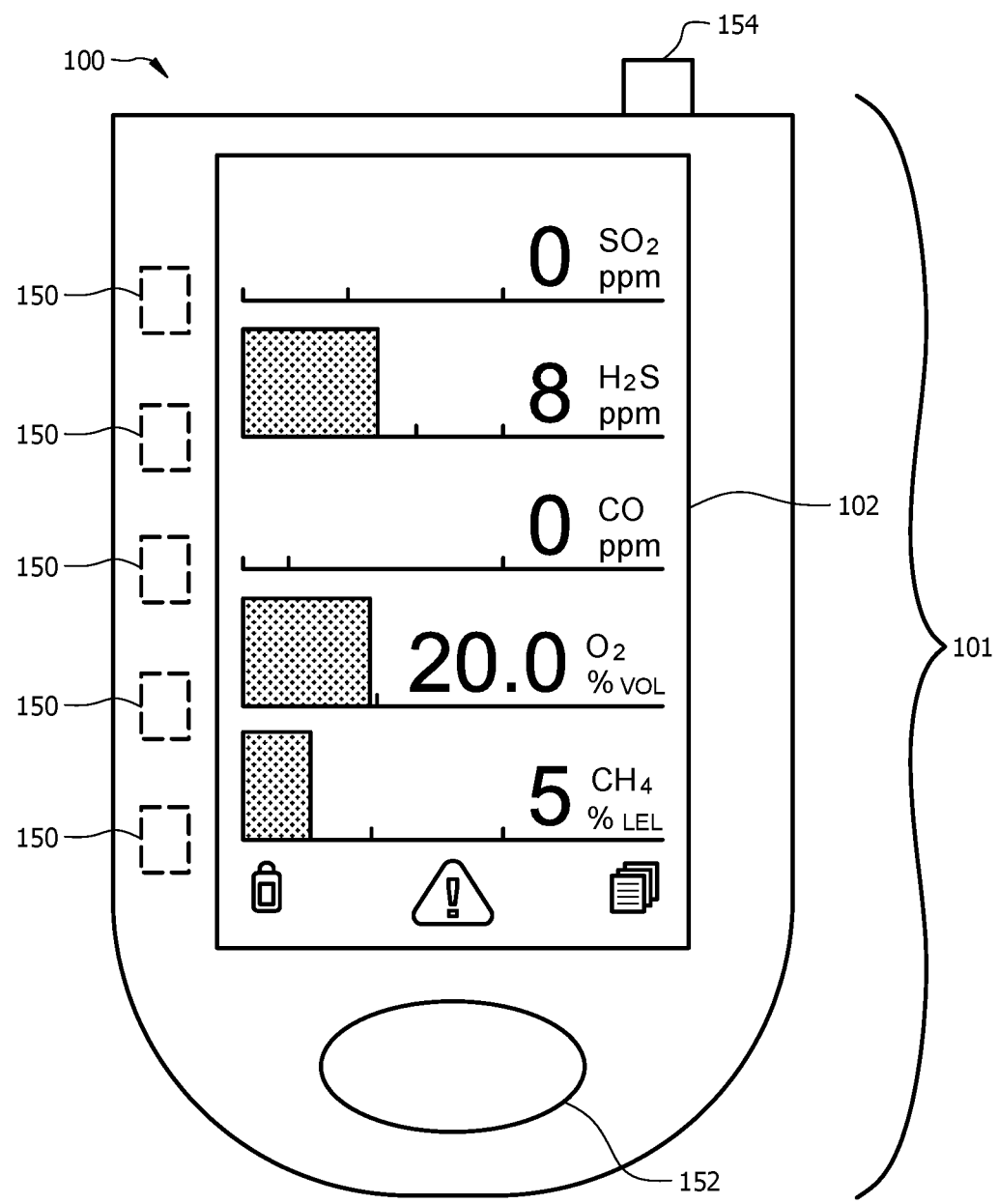
FIG. 1 illustrates a gas detector according to an embodiment of the disclosure.

It should be understood at the outset that although illustrative implementations of one or more embodiments are illustrated below, the disclosed systems and methods may be implemented using any number of techniques, whether currently known or not yet in existence. The disclosure should in no way be limited to the illustrative implementations, drawings, and techniques illustrated below, but may be modified within the scope of the appended claims along with their full scope of equivalents.

The following brief definition of terms shall apply throughout the application:

The term "comprising" means including but not limited to, and should be interpreted in the manner it is typically used in the patent context;

The phrases "in one embodiment," "according to one embodiment," and the like generally mean that the particular feature, structure, or characteristic following the phrase may be included in at least one embodiment of the present invention, and may be included in more than one embodiment of the present invention (importantly, such phrases do not necessarily refer to the same embodiment);

If the specification describes something as "exemplary" or an "example," it should be understood that refers to a non-exclusive example;

The terms "about" or "approximately" or the like, when used with a number, may mean that specific number, or alternatively, a range in proximity to the specific number, as understood by persons of skill in the art field; and If the specification states a component or feature "may," "can," "could," "should," "would," "preferably," "possibly," "typically," "optionally," "for example," "often," or "might" (or other such language) be included or have a characteristic, that particular component or feature is not required to be included or to have the characteristic. Such component or feature may be optionally included in some embodiments, or it may be excluded.

Embodiments of the disclosure include systems and methods for controlling the display of a gas detector device. In some embodiments, the gas detector device may be configured to display alarms or alerts to a user based on the data received by sensors within the gas detector. The alarms or alerts may comprise information about the received data, including current reading, exceeded limits, type of alarm, etc.

Current policies and protocols during a gas alarm situation are to evacuate the potentially hazardous area and investigate later, even if it is a false alarm. Some novice employees may not be aware of the details associated with an alarm, such as the set-point or threshold, so a numeral representation may not be helpful to that user. Therefore, they may rely on the gas detector to provide them with the right feedback to react in an emergency. Some senior employees may be likely to ignore or dismiss an alarm, or assume it is a false alarm. They may be likely to analyze the sensor data available on the gas detector device, including information not associated with the alarm, before deciding to evacuate. If the alarm is not a false alarm, the delay in evacuation could result in potential injury or casualties.

Using methods and systems disclosed herein, a supervisor may have the opportunity to limit the amount of information available to an employee during an alarm, such that the employee has the right information in the right moment. Limiting the information available on the display of a gas detector during an alarm may prevent delay or confusion before the user evacuates. In some embodiments, the system may be called "Only Alert" as it allows only the alarm or alert information to be displayed. The use of this system may benefit both novice and expert users when the protocol for response to an alarm is to evacuate first.

Typical gas detectors may show all gas sensor information at all times, including during a gas alarm situation. While limiting the information may not be beneficial for all users, such as supervisors who need to assess the alarm situation, most workers do not need access to all of the information in order to appropriately respond to an alarm situation.

Only Alert may be a user controlled feature, via software on the gas detector. In some embodiments, an Only Alert system may be implemented into existing gas detector devices by updating the software of the device. When the Only Alert system is enabled and a gas alarm situation occurs, the gas detector display will only show the alarm gas channel information, omitting the rest.

A gas detector device (such as the gas detector 100 shown in FIG. 1) using Only Alert may comprise a plurality of sensors 150 (or channels) configured to provide information about a plurality of gases and/or conditions, for example, oxygen levels, combustibles, and/or toxic gases. In some embodiments, the gas detector device 100 may comprise a user interface 101 comprising a display 102 configured to display information for at least two sensors or channels. In some embodiments, the gas detector 100 may comprise other user interface elements, such as buttons 152, indicators 154, sound generators, etc. The gas detector 100 may be designed for continuous and/or periodic monitoring, and may be mobile to be carried by a user. In some embodiments, exemplary gas detectors may be used in underground utilities vaults, boiler rooms, industrial plants, chemical plants, refineries, and other similar work environments.

In some embodiments, the gas detector may comprise a controller, which may be processor, microprocessor, or other similar device, where the controller may be included in any of the embodiments disclosed herein. The controller may be capable of sending and receiving signals, displays, and other data. The controller may be configured to process data, format data, among other functions. The controller may comprise a memory, where the memory may store an application that can execute all the steps described in the disclosed embodiments.

Referring now to FIGS. 2A-2C, exemplary gas detector displays are shown, wherein the display may be part of a user interface 101 for the gas detector 100 (shown in FIG. 1). In the embodiments shown in FIGS. 2A-2C, the gas detector may be in normal operating mode, and may not have any alarms or alerts.

FIG. 2A shows a first example of a gas detector display 102, wherein the display 102 includes sections of information for a plurality of gases. The display includes a first section 111, second section 112, third section 113, fourth section 114, and fifth section 115, wherein each of the sections contains information about different sensor readings or data. In some embodiments, the sections may contain gas identification as well as the current reading for that gas. In some embodiments, the display 102 may comprise a general information section 140 comprising information such as battery life remaining, current time, access to other sections or displays, among other things. In some embodiments, the general information section 140 may be located at the bottom of the display 102. In other embodiments, the general information section 140 may be located in another location within the display 102.

FIG. 2B shows a second example of a gas detector display 104, wherein the display 104 includes sections of information for a plurality of gases. The display includes a first section 121, second section 122, third section 123, and fourth section 124, wherein each of the sections contains information about different sensor readings or data. In some embodiments, the sections may contain gas identification as well as the current reading for that gas. In some embodiments, the display 104 may comprise a general information section 140 comprising information such as battery life remaining, current time, access to other sections or displays, among other things. In some embodiments, the general information section 140 may be located at the bottom of the display 104. In other embodiments, the general information section 140 may be located in another location within the display 104.

FIG. 2C shows a third example of a gas detector display 106, wherein the display 106 includes sections of information for a plurality of gases. The display includes a first section 131, second section 132, third section 133, fourth section 134, and fifth section 135, wherein each of the sections contains information about different sensor readings or data. In some embodiments, the sections may contain gas identification as well as the current reading for that gas. In some embodiments, the display 106 may comprise a general information section 140 comprising information such as battery life remaining, current time, access to other sections or displays, among other things. In some embodiments, the general information section 140 may be located at the bottom of the display 106. In other embodiments, the general information section 140 may be located in another position within the display 106.

Figure 3A:
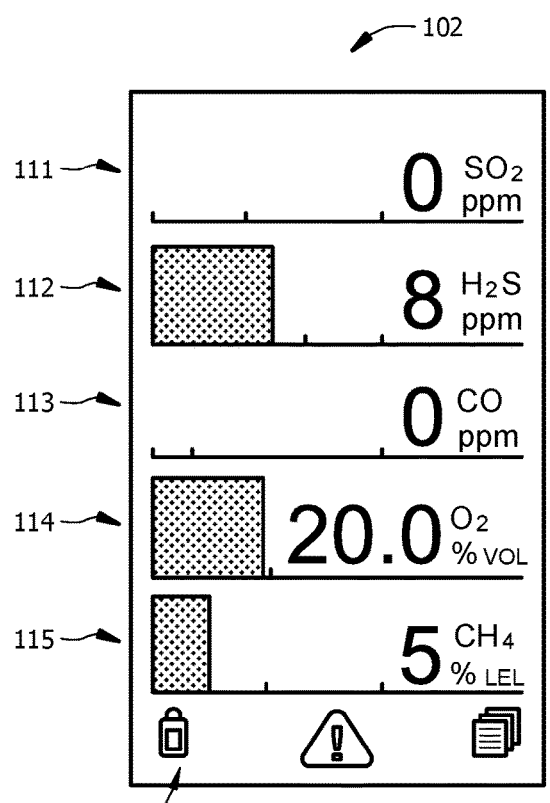
FIGS. 3A-3B illustrate display and alarm screens for a gas detector according to an embodiment of the disclosure.
Figure 3B:
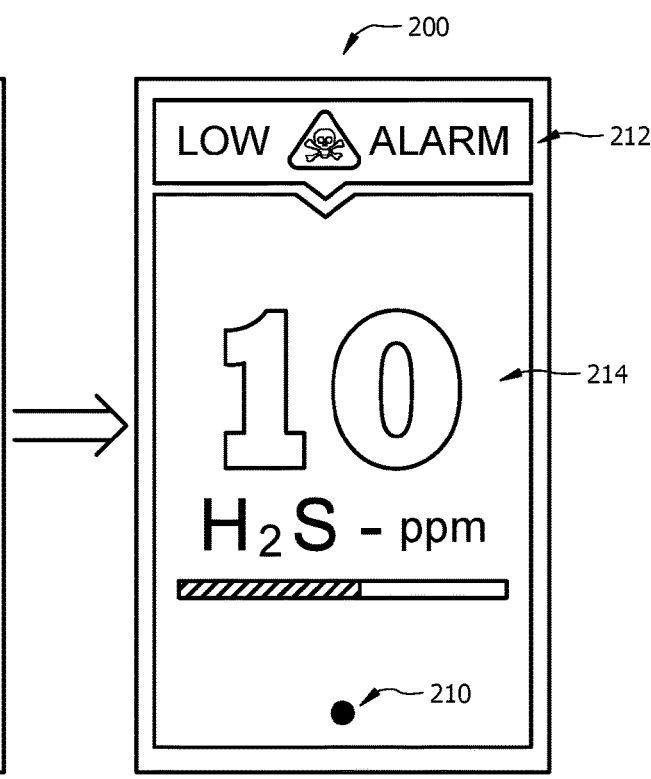

Referring now to FIGS. 3A-3B, an exemplary method for controlling the display 102 when an alarm is received, or registered, by the gas detector is shown. When an alarm status is registered by the gas detector, the display 102 showing all of the plurality of gas readings may switch to an alarm screen 200 comprising only the alarm information. In some embodiments, the alarm screen 200 may comprise an alarm identifier 212, a current reading 214, as well as other information about the alarm. In some embodiments, the alarm screen 200 may comprise an indicator 210 for the number of alarm screens (explained in more detail below). The alarm screen 200 may be designed to provide only the critical information to a user, avoiding confusion or delay when the user is in a hazardous environment. For example, if a display contained all of the information shown in the normal operation display 102, the user may spend more time attempting to decipher the alarm. Therefore, the alarm screen 200 may comprise only the critical information associated with the alarm, and the user may be able to adequately respond to the alert or alarm without distraction.

Figures 4A, 4B:
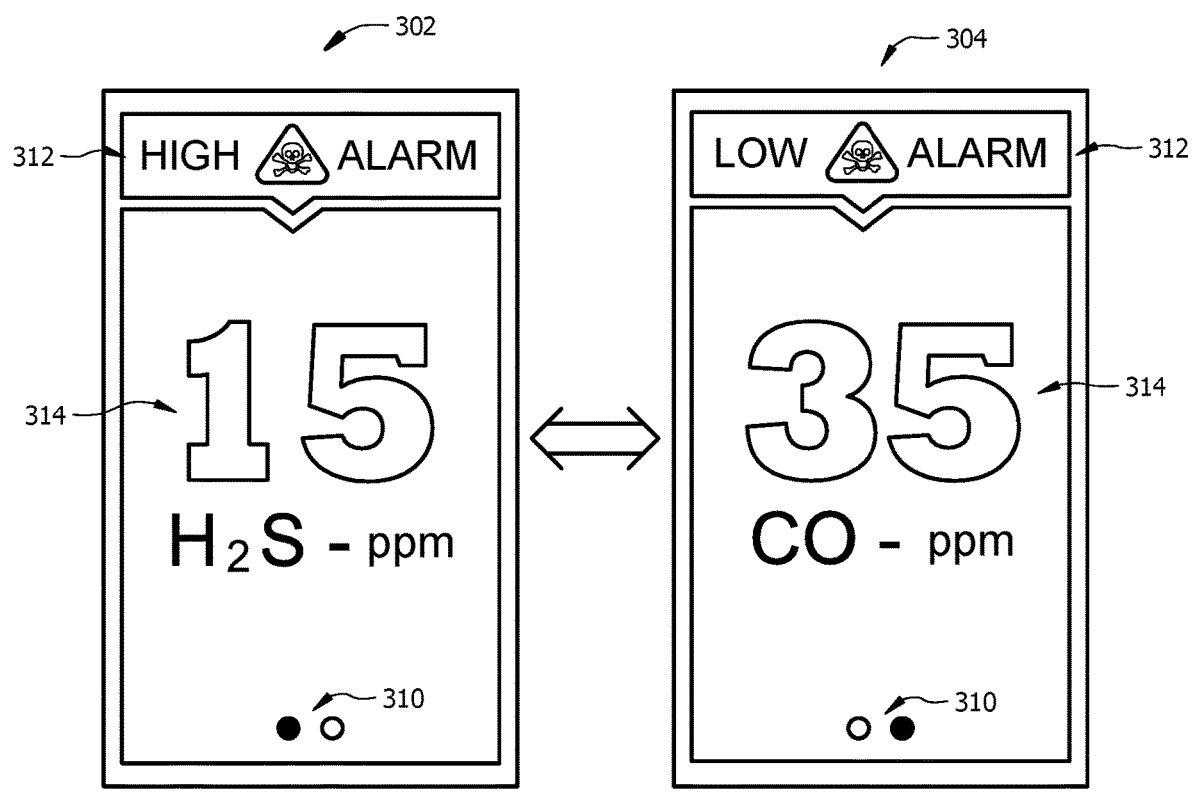
FIGS. 4A-4B illustrate alarm screens for a gas detector according to an embodiment of the disclosure.

Referring now to FIGS. 4A-4B, an embodiment is shown where there is more than one alarm detected by the gas detector. As described in FIGS. 3A-3B, when an alarm is registered, the normal operating display may switch to a full screen alarm display (or a first alarm screen 302). Then, if more than one alarm is issued, a second alarm screen 304 may be generated, where the first alarm screen 302 and second alarm screen 304 may be shown alternatively by the display of the gas detector. In the embodiment shown in FIGS. 4A-4B, the alarm screens may comprise an alarm identifier 312, a current reading 314, as well as other information about the alarm. In some embodiments, the alarm screens 302, 304 may comprise an indicator 310 for the number of alarm screens (two in this case). The indicator 310 may also highlight which screen is currently being shown on the display.

Showing the alarm screens 302, 304 as full screen displays that alternate may limit confusion and delay on the part of the user, while still providing critical information to the user. In some embodiments, the alarm screens 302 and 304 may switch at predetermined time intervals. In some embodiments, a user may press a button to switch between the two alarm screens 302 and 304.

Referring now to FIGS. 5A-5C, an embodiment is shown where there is more than one alarm detected by the gas detector. As described in FIGS. 3A-3B, when an alarm is registered, the normal operating display may switch to a full screen alarm display (or a first alarm screen 402). Then, if more than one alarm is issued, a second alarm screen 404 may be generated, and a third alarm screen 406 may be generated, where the first alarm screen 402, second alarm screen 404, and third alarm screen 406 may be shown alternatively by the display of the gas detector. In the embodiment shown in FIGS. 5A-5C, the alarm screens may comprise an alarm identifier 412, a current reading 414, as well as other information about the alarm. In some embodiments, the alarm screens may comprise an indicator 410 for the number of alarm screens (three in this case). The indicator 410 may also highlight which screen is currently being shown on the display.

Showing the alarm screens 402, 404, and 406 as full screen displays that alternate may limit confusion and delay on the part of the user, while still providing critical information to the user. In some embodiments, the alarm screens 402, 404, and 406 may switch at predetermined time intervals. In some embodiments, a user may press a button to switch between the three alarm screens 402, 404, and 406.

Some embodiments of the disclosure may comprise a gas detector configured to detect multiple gases, the gas detector comprising a plurality of sensors configured to detect a plurality of gases and conditions; a user interface comprising a display configured to display information received from the plurality of sensors; wherein when the gas detector is in normal operating mode, the display includes information for more than one of the plurality of sensors, and wherein when the gas detector is in an alarm or alert mode, the display changes to an alarm screen that includes only the alarm information.

In some embodiments, the alarm information comprises a single alarm or alert. In some embodiments, the alarm information comprises a plurality of alarms or alerts, and wherein the display is configured to switch between the alarm screens for each of the plurality of alarms. In some embodiments, the display automatically switches between the plurality of alarm screens at predefined time intervals. In some embodiments, the display switches between the plurality of alarm screens when a user presses a button. In some embodiments, the display is configured to indicate the number of alarm screens currently existing on the gas detector. In some embodiments, the alarm screen comprises a full screen display. In some embodiments, the alarm screen includes the type of alarm and current reading for that sensor. In some embodiments, the gas detector is configured to detect $SO_2$, $H_2S$, $CO$, $O_2$, and $CH_4$. In some embodiments, the display is further configured to switch back to the normal operating mode when the alarm mode is deactivated.

Some embodiments of the disclosure include a method for controlling the display of a gas detector comprising receiving sensed data from a plurality of sensors of the gas detector; displaying the received sensed data on a user interface of the gas detector, wherein the user interface comprises a display, and wherein the display includes information for more than one of the plurality of sensors; and changing the display to an alarm screen that includes only the alarm information, when the gas detector is in an alarm or alert mode.

In some embodiments, the method may further comprise, when the alarm information comprises a plurality of alarms or alerts, switching between a plurality of alarm screens for each of the plurality of alarms. In some embodiments, switching between the plurality of alarm screens comprises automatically switching between the plurality of alarm screens at predefined time intervals. In some embodiments, switching between the plurality of alarm screens comprises switching between the plurality of alarm screens when a user presses a button. In some embodiments, the method may further comprise indicating, by the display, the number of alarm screens currently existing on the gas detector. In some embodiments, the alarm screen comprises a full screen display. In some embodiments, the alarm screen includes the type of alarm and current reading for that sensor. In some embodiments, the method may further comprise changing the display from the alarm screen to a normal operating screen, when the gas detector is no longer in alarm or alert mode, wherein the normal operating screen includes information for more than one of the plurality of sensors.

In an embodiment, a gas detector may comprise a plurality of sensors configured to detect a plurality of characteristics of the ambient environment; a user interface comprising a display; and a controller configured to receive sensed data from the plurality of sensors; display the received sensed data via the display of the user interface, wherein the display includes information for more than one of the plurality of sensors; and change the display to an alarm screen that includes only alarm information, when the gas detector is in an alarm mode.

In some embodiments, the alarm information comprises a plurality of alarms or alerts, and wherein the display is configured to switch between a plurality of alarm screens for each of the plurality of alarms. In some embodiments, the controller is further configured to automatically switch between the plurality of alarm screens at predefined time intervals. In some embodiments, the controller is further configured to indicate the number of alarm screens currently existing on the gas detector. In some embodiments, the controller is configured to switch back to a normal operating mode when the alarm mode is deactivated.

While various embodiments in accordance with the principles disclosed herein have been shown and described above, modifications thereof may be made by one skilled in the art without departing from the spirit and the teachings of the disclosure. The embodiments described herein are representative only and are not intended to be limiting. Many variations, combinations, and modifications are possible and are within the scope of the disclosure. Alternative embodiments that result from combining, integrating, and/or omitting features of the embodiment(s) are also within the scope of the disclosure. Accordingly, the scope of protection is not limited by the description set out above, but is defined by the claims which follow, that scope including all equivalents of the subject matter of the claims. Each and every claim is incorporated as further disclosure into the specification and the claims are embodiment(s) of the present invention(s). Furthermore, any advantages and features described above may relate to specific embodiments, but shall not limit the application of such issued claims to processes and structures accomplishing any or all of the above advantages or having any or all of the above features.

Additionally, the section headings used herein are provided for consistency with the suggestions under 37 C.F.R. 1.77 or to otherwise provide organizational cues. These headings shall not limit or characterize the invention(s) set out in any claims that may issue from this disclosure. Specifically and by way of example, although the headings might refer to a "Field," the claims should not be limited by the language chosen under this heading to describe the so-called field. Further, a description of a technology in the "Background" is not to be construed as an admission that certain technology is prior art to any invention(s) in this disclosure. Neither is the "Summary" to be considered as a limiting characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of the claims shall be considered on their own merits in light of this disclosure, but should not be constrained by the headings set forth herein.

Use of broader terms such as "comprises," "includes," and "having" should be understood to provide support for narrower terms such as "consisting of," "consisting essentially of," and "comprised substantially of." Use of the terms "optionally," "may," "might," "possibly," and the like with respect to any element of an embodiment means that the element is not required, or alternatively, the element is required, both alternatives being within the scope of the embodiment(s). Also, references to examples are merely provided for illustrative purposes, and are not intended to be exclusive.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted or not implemented.

Also, techniques, systems, subsystems, and methods described and illustrated in the various embodiments as discrete or separate may be combined or integrated with other systems, modules, techniques, or methods without departing from the scope of the present disclosure. Other items shown or discussed as directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein.

What is claimed is:

1. A gas detector configured to detect multiple gases, the gas detector comprising:
   a plurality of sensors configured to detect a plurality of gases and conditions; and
   a user interface comprising a display configured to display information received from the plurality of sensors, wherein:
      when the gas detector is in a normal operating mode, the display includes information for more than one of the plurality of sensors when all information for the plurality of sensors is within a predetermined limit; and
      when the gas detector is in an alarm or alert mode, the display changes from the normal operating mode to an alarm screen that includes only alarm information and omits any information for the plurality of sensors that is within the predetermined limit in response to information from at least one of the plurality of sensors exceeding the predetermined limit, wherein the alarm information includes the information for the at least one of the plurality of sensors exceeding the predetermined limit.

2. The gas detector of claim 1, wherein the alarm information comprises a single alarm or alert.

3. The gas detector of claim 1, wherein the alarm information comprises a plurality of alarms or alerts, and wherein the display is configured to switch between alarm screens for each of the plurality of alarms or alerts.

4. The gas detector of claim 3, wherein the display is configured to automatically switch between the alarm screens at predefined time intervals.

5. The gas detector of claim 3, wherein the display is configured to switch between the alarm screens in response to a user pressing a button.

6. The gas detector of claim 3, wherein the display is configured to indicate a number of alarm screens currently existing on the gas detector.

7. The gas detector of claim 1, wherein the alarm screen includes a type of alarm and a current reading for that sensor.

8. The gas detector of claim 1, wherein the gas detector is configured to detect one or more of the following: sulfur dioxide ($SO_2$), hydrogen sulfide ($H_2S$), carbon monoxide (CO), oxygen ($O_2$), and methane ($CH_4$).

9. The gas detector of claim 1, wherein the display is configured to switch back to the normal operating mode when the alarm or alert mode is deactivated.

10. A method for controlling a display of a gas detector comprising:
    receiving sensed data from a plurality of sensors of the gas detector;
    displaying the received sensed data via a user interface of the gas detector, wherein the user interface comprises a display, and wherein the display includes information for more than one of the plurality of sensors when all information for the plurality of sensors is within a predetermined limit; and
    changing the display to an alarm screen that includes only alarm information and omits any information for the plurality of sensors that is within the predetermined limit in response to information from at least one of the plurality of sensors exceeding the predetermined limit, when the gas detector is in an alarm or alert mode, based on the received sensed data exceeding the predetermined limit corresponding to at least one of the plurality of sensors.

11. The method of claim 10, further comprising, when the alarm information comprises a plurality of alarms or alerts, switching between a plurality of alarm screens for each of the plurality of alarms or alerts.

12. The method of claim 11, wherein switching between the plurality of alarm screens comprises automatically switching between the plurality of alarm screens at predefined time intervals.

13. The method of claim 11, wherein switching between the plurality of alarm screens comprises switching between the plurality of alarm screens when a user presses a button.

14. The method of claim 11, further comprising indicating, via the display, a number of alarm screens currently existing on the gas detector.

15. The method of claim 10, further comprising changing the display from the alarm screen to a normal operating screen, when the gas detector is no longer in the alarm or alert mode, wherein the normal operating screen includes information for the more than one of the plurality of sensors.

16. A gas detector comprising:
   a plurality of sensors configured to detect a plurality of characteristics of an ambient environment;
   a user interface comprising a display; and
   a controller configured to:
      receive sensed data from the plurality of sensors;
      display the received sensed data via the display of the user interface, wherein the display includes information for more than one of the plurality of sensors when the gas detector is in a normal operating mode, wherein the display includes information for more than one of the plurality of sensors when all information for the plurality of sensors is within a predetermined limit; and
      change the display to an alarm screen that includes only alarm information when the gas detector is in an alarm mode, and omits any information for the plurality of sensors that is within the predetermined limit in response to information from at least one of the plurality of sensors exceeding the predetermined limit, wherein the alarm information includes information for the plurality of sensors exceeding the predetermined limit.

17. The gas detector of claim 16, wherein the alarm information comprises a plurality of alarms or alerts, and wherein the display is configured to switch between a plurality of alarm screens for each of the plurality of alarms or alerts.

18. The gas detector of claim 17, wherein the controller is further configured to automatically switch between the plurality of alarm screens at predefined time intervals.

19. The gas detector of claim 16, wherein the controller is further configured to indicate a number of alarm screens currently existing on the gas detector.

20. The gas detector of claim 16, wherein the controller is configured to switch back to the normal operating mode when the alarm mode is deactivated.

* * * * *